(12) United States Patent
Govari (10) Patent No.: US 9,364,285 B2
(45) Date of Patent: Jun. 14, 2016

(54) SEALED TWO-WAY MAGNETIC MANIFOLD (71) Applicant: BIOSENSE WEBSTER (ISRAEL) LTD., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 4 days.

(21) Appl. No.: 14/231,812

(22) Filed: Apr. 1, 2014

(65) Prior Publication Data
US 2015/0272665 A1 Oct. 1, 2015

(51) Int. Cl.
*A61B 18/14* (2006.01)
*A61M 3/02* (2006.01)
*A61B 18/00* (2006.01)

(52) U.S. Cl.
CPC .......... *A61B 18/1492* (2013.01); *A61M 3/0279* (2013.01); *A61B 2018/00011* (2013.01); *A61B 2018/00029* (2013.01); *A61B 2018/00351* (2013.01); *A61B 2018/00714* (2013.01); *A61B 2018/00744* (2013.01); *A61B 2018/1467* (2013.01); *A61B 2218/002* (2013.01); *A61M 2205/054* (2013.01); *A61M 2205/50* (2013.01)

(58) Field of Classification Search
CPC ................. A61B 18/1492; A61B 2018/00744; A61M 5/16827; F16K 27/067; F16K 5/065; F16K 31/0665; F16K 15/04; F16K 15/183
See application file for complete search history.

(56) References Cited

U.S. PATENT DOCUMENTS 3,916,948 A * 11/1975 Benjamin ..................... 137/861
4,103,686 A 8/1978 Lefevre
5,391,199 A 2/1995 Ben-Haim
5,443,489 A 8/1995 Ben-Haim
5,527,295 A 6/1996 Wing
5,558,091 A 9/1996 Acker et al.
5,904,669 A 5/1999 Schildgen
5,944,022 A 8/1999 Nardella et al.
5,983,126 A 11/1999 Wittkampf
6,066,088 A * 5/2000 Davis .............................. 600/29
6,071,280 A * 6/2000 Edwards et al. ................ 606/41
6,172,499 B1 1/2001 Ashe
6,177,792 B1 1/2001 Govari et al.

(Continued)

FOREIGN PATENT DOCUMENTS

GB 2190983 A 12/1987

OTHER PUBLICATIONS

European Search Report for application dated Sep. 4, 2015, for Application No. EP15162069.

*Primary Examiner* — Bradley Osinski
(74) *Attorney, Agent, or Firm* — Notaro, Michalos & Zaccaria P.C.

(57) ABSTRACT

An irrigated medical device, including an inlet tube configured to receive an irrigation fluid from a pressurized fluid source, at least first and second outlet tubes configured to deliver the irrigation fluid to respective outlets of the device, a manifold containing a chamber coupled between the inlet tube and at least the first and second outlet tubes, and a ball including a magnetic material contained inside the chamber. The irrigated medical device also includes a magnetic field generator disposed outside the chamber and configured to generate a variable magnetic field within the chamber so as to move the ball between at least a first position in which the first outlet tube is blocked, a second position in which the second outlet tube is blocked, and a third position, in which neither of the outlet tubes is blocked.

6 Claims, 5 Drawing Sheets

(56) References Cited

U.S. PATENT DOCUMENTS

| | | |
|---|---|---|
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 2009/0093806 A1 | 4/2009 | Govari et al. |
| 2009/0138007 A1 | 5/2009 | Govari et al. |
| 2010/0137859 A1 | 6/2010 | Wang |

* cited by examiner

SEALED TWO-WAY MAGNETIC MANIFOLD

FIELD OF THE INVENTION

The present invention relates generally to invasive probes, and specifically to a manifold that can direct irrigation fluid to specific irrigation apertures in the probe.

BACKGROUND OF THE INVENTION

A wide range of medical procedures involve placing objects such as sensors, tubes, catheters, dispensing devices, and implants, within the body. An example of a medical procedure performed with a catheter is ablation of body tissue such as heart tissue. The ablation may be used to cure a variety of cardiac arrhythmia such as atrial fibrillation. Such procedures are known in the art. Other medical procedures using ablation of body tissue, such as treating varicose veins, are also known in the art. The ablation energy for these procedures may be in the form of radio-frequency (RF) energy, which is supplied to the tissue via one or more electrodes of a catheter used for the procedures.

The application of the ablation energy to body tissue, if uncontrolled, may lead to an unwanted increase of temperature of the tissue. It is consequently important to monitor and control the temperature of the tissue during any medical procedure involving ablation. One method for control is to irrigate the tissue being ablated.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention an irrigated medical device, including an inlet tube configured to receive an irrigation fluid from a pressurized fluid source, at least first and second outlet tubes configured to deliver the irrigation fluid to respective outlets of the device, a manifold containing a chamber coupled between the inlet tube and at least the first and second outlet tubes, a ball including a magnetic material contained inside the chamber, and a magnetic field generator disposed outside the chamber and configured to generate a variable magnetic field within the chamber so as to move the ball between at least a first position in which the first outlet tube is blocked, a second position in which the second outlet tube is blocked, and a third position, in which neither of the outlet tubes is blocked.

In some embodiments, the respective outlets are connected to respective apertures of multiple ablation electrodes. In additional embodiments, the irrigation fluid may include a saline solution. In further embodiments, the magnetic material may include steel.

In supplemental embodiments, the magnetic field generator may include multiple electromagnets disposed outside the chamber. In some embodiments, the magnetic field generator can be configured to generate the variable magnetic field by activating a given electromagnet.

There is also provided, in accordance with an embodiment of the present invention a method, including inserting, into a body cavity, a distal end of a insertion tube, the insertion tube coupled to a medical device including an inlet tube configured to receive an irrigation fluid from a pressurized fluid source, at least first and second outlet tubes configured to deliver the irrigation fluid to respective outlets of the device, a manifold containing a chamber coupled between the tube and at least the first and second outlet tubes, and a ball including a magnetic material contained inside the chamber, and a magnetic field generator disposed outside the chamber. The method also includes generating, by the magnetic field generator, a variable magnetic field within the chamber so as to move the ball between at least a first position in which the first outlet tube is blocked, a second position in which the second outlet tube is blocked, and a third position, in which neither of the outlet tubes is blocked.

There is further provided, in accordance with an embodiment of the present invention a computer software product, operated in conjunction with a probe that is configured for insertion into a body cavity of a patient and a medical device including an inlet tube configured to receive an irrigation fluid from a pressurized fluid source and at least first and second outlet tubes configured to deliver the irrigation fluid to respective outlets of the device. The medical device also includes a manifold containing a chamber coupled between the inlet tube and at least the first and second outlet tubes, a ball including a magnetic material contained inside the chamber, and a magnetic field generator disposed outside the chamber. The product includes a non-transitory computer-readable medium, in which program instructions are stored, which instructions, when read by a computer, cause the magnetic field generator to generate a variable magnetic field within the chamber so as to move the ball between at least a first position in which the first outlet tube is blocked, a second position in which the second outlet tube is blocked, and a third position, in which neither of the outlet tubes is blocked.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Various therapeutic procedures such as cardiac ablation use an invasive medical probe such as a catheter that is inserted into a patient's body. During an ablation procedure on a heart, there may be local overheating of the heart surface being ablated, as well as of the heart tissue underlying the surface. The surface overheating may be manifested as charring, and the overheating of the underlying tissue may cause other damage to the tissue, even leading to penetration of the tissue. To control the temperature of the surface and the underlying tissue, the region being ablated may be irrigated with an irrigation fluid, typically saline, in order to prevent charring.

In addition to the risk of charring, overheating of blood in the region being ablated may cause the formation of potentially dangerous blood clots, which can grow and potentially cause a heart attack or a stroke. In some cases the irrigation may reduce blood clot formation by cooling and diluting the blood.

Some catheters are configured with multiple ablation electrodes having respective apertures to deliver irrigation fluid to the tissue. While a first ablation electrode is ablating the tissue, its respective apertures may be blocked by the tissue, thereby causing much of the irrigation fluid to flow through apertures of a second ablation electrode. Embodiments of the present invention provide a medical device for directing irrigation fluid to the respective apertures of one or more of the ablation electrodes, thereby ensuring that the correct region is irrigated.

In some embodiments, the medical device comprises a manifold coupled between an inlet tube and at least first and second outlet tubes. As described hereinbelow, the inlet tube is configured to receive an irrigation fluid from a pressurized fluid source, and the outlet tubes are configured to deliver the irrigation fluid to respective outlets of the device.

In some embodiments, a ball comprising a magnetic material is contained inside the chamber, and a magnetic field generator is disposed outside the chamber and configured to generate a variable magnetic field within the chamber so as to move the ball between at least a first position in which the first outlet tube is blocked, a second position in which the second outlet tube is blocked, and a third position, in which neither of the outlet tubes is blocked.

System Description

Figure 1:
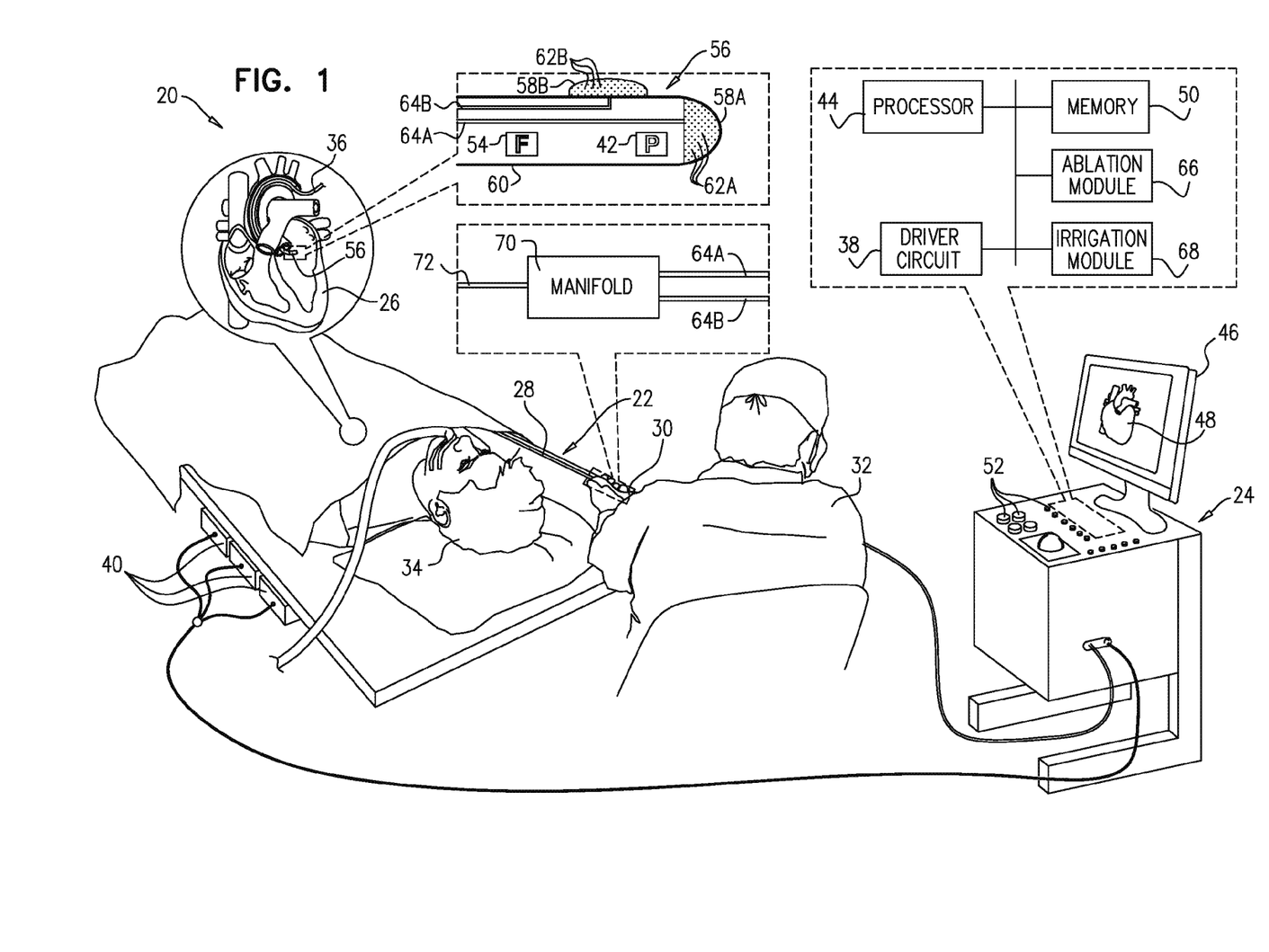
FIG. 1 is a schematic pictorial illustration of a medical system comprising a manifold configured to control flow of an irrigation fluid, in accordance with an embodiment of the present invention.

FIG. 1 is a schematic pictorial illustration of a medical system 20, in accordance with an embodiment of the present invention. System 20 may be based, for example, on the CARTO™ system, produced by Biosense Webster Inc. (Diamond Bar, Calif.). System 20 comprises a probe 22, such as a catheter, and a control console 24. In the embodiment described hereinbelow, it is assumed that probe 22 is used for diagnostic or therapeutic treatment, such as performing ablation of heart tissue in a heart 26. Alternatively, probe 22 may be used, mutatis mutandis, for other therapeutic and/or diagnostic purposes in the heart or in other body organs.

Probe 22 comprises a flexible insertion tube 28, and a handle 30 coupled to a proximal end of the insertion tube. By manipulating handle 30, an operator 32 can insert probe 22 into a body cavity in a patient 34. For example, operator 32 can insert probe 22 through the vascular system of a patient 34 so that a distal end 36 of probe 22 enters a chamber of heart 26 and engages endocardial tissue at a desired location or locations.

System 20 typically uses magnetic position sensing to determine position coordinates of distal end 36 inside heart 26. Console 24 comprises a driver circuit 38 which drives field generators 40 to generate magnetic fields within the body of patient 34. Typically, field generators 40 comprise coils, which are placed below the patient's torso at known positions external to patient 34. These coils generate magnetic fields in a predefined working volume that contains heart 26. A magnetic field sensor 42 (also referred to herein as position sensor 42) within distal end 36 of probe 22 generates electrical signals in response to the magnetic fields from the coils, thereby enabling console 24 to determine the position of distal end 36 within the chamber.

Although in the present example system 20 measures the position of distal end 36 using magnetic-based sensors, other position tracking techniques may be used (e.g., impedance-based sensors). Magnetic position tracking techniques are described, for example, in U.S. Pat. Nos. 5,391,199, 6,690,963, 5,443,489, 6,788,967, 5,558,091, 6,172,499 and 6,177,792, whose disclosures are incorporated herein by reference. Impedance-based position tracking techniques, are described, for example, in U.S. Pat. Nos. 5,983,126, 6,456,864 and 5,944,022, whose disclosures are incorporated herein by reference. Both systems generate signals which vary according to the position of distal end 36.

A processor 44 processes these signals in order to determine the position coordinates of distal end 36, typically including both location and orientation coordinates. The method of position sensing described hereinabove is implemented in the above-mentioned CARTO™ system and is described in detail in the patents and patent applications cited above.

Processor 44 typically comprises a general-purpose computer, with suitable front end and interface circuits for receiving signals from probe 22 and controlling the other components of console 24. Processor 44 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 44 may be carried out by dedicated or programmable digital hardware components.

Based on the signals received from probe 22 and other components of system 20, processor 44 drives a display 46 to present operator 32 with an image 48 showing the position of distal end 36 in the patient's body, as well as status information and guidance regarding the procedure that is in progress. Processor 44 stores data representing image 48 in a memory 50. In some embodiments, operator 32 can manipulate image 48 using one or more input devices 52.

Probe 22 also comprises a force sensor 54 contained within distal end 36. Force sensor 54 measures a force applied by a distal tip 56 of probe 22 to the endocardial tissue of heart 26 by generating a signal to the console that is indicative of the force exerted by the distal tip on the endocardial tissue. In one embodiment, the force sensor may comprise a magnetic field transmitter and receiver connected by a spring in distal tip 56, and may generate an indication of the force based on measuring the deflection of the spring. Further details of this sort of probe and force sensor are described in U.S. Patent Application Publications 2009/0093806 and 2009/0138007, whose disclosures are incorporated herein by reference. Alternatively, distal end 32 may comprise another type of force sensor.

In the present embodiment, electrodes 58 are mounted on distal end 36. Electrodes 58 typically comprise thin metal layers formed over an insulating sheath 60 of insertion tube 28. In the configuration shown in FIG. 1, each electrode 58 has one or more respective irrigation apertures 62 and a respective outlet tube 64 that is configured to supply irrigation fluid through the one or more apertures in distal end 36, as described hereinbelow. In the example shown in FIG. 1, electrodes 58, apertures 62, and outlet tubes 64 may be differentiated by appending a letter to the identifying numeral so that the electrodes comprise electrodes 58A and 58B. Electrode 58A has apertures 62A and is in fluid communication with outlet tube 64A, and electrode 58B has apertures 62B and is in fluid communication with outlet tube 64B.

Console 24 also comprises a radio frequency (RF) ablation module 66 and an irrigation module 68. Processor 44 uses the ablation module to monitor and control ablation parameters such as the level of ablation power applied via electrodes 58. The ablation module may also monitor and control the duration of the ablation that is provided.

Typically, during ablation, heat is generated in one or more of the electrodes providing the ablation, as well as in the surrounding region. In order to dissipate the heat and to improve the efficiency of the ablation process, system 20 supplies irrigation fluid to distal end 36 via an inlet tube 72. System 20 uses irrigation module 68 as a pressurized fluid source that monitors and controls irrigation parameters, such as the pressure and the temperature of the irrigation fluid. The irrigation fluid is typically normal saline solution, and the rate of flow of the fluid, controlled by irrigation module 68, is typically in the range of approximately 10-20 cc/minute, but may be higher or lower than this range.

As described in detail hereinbelow, a manifold 70 controls the flow of the irrigation fluid from inlet tube 72 to outlet tube 64A and/or outlet tube 64B. While the configuration in FIG. 1 shows manifold 70 positioned in handle 30, the manifold may be positioned in any part of system 20. For example, the manifold may be positioned within insertion tube 28 or within console 24.

Figure 2:
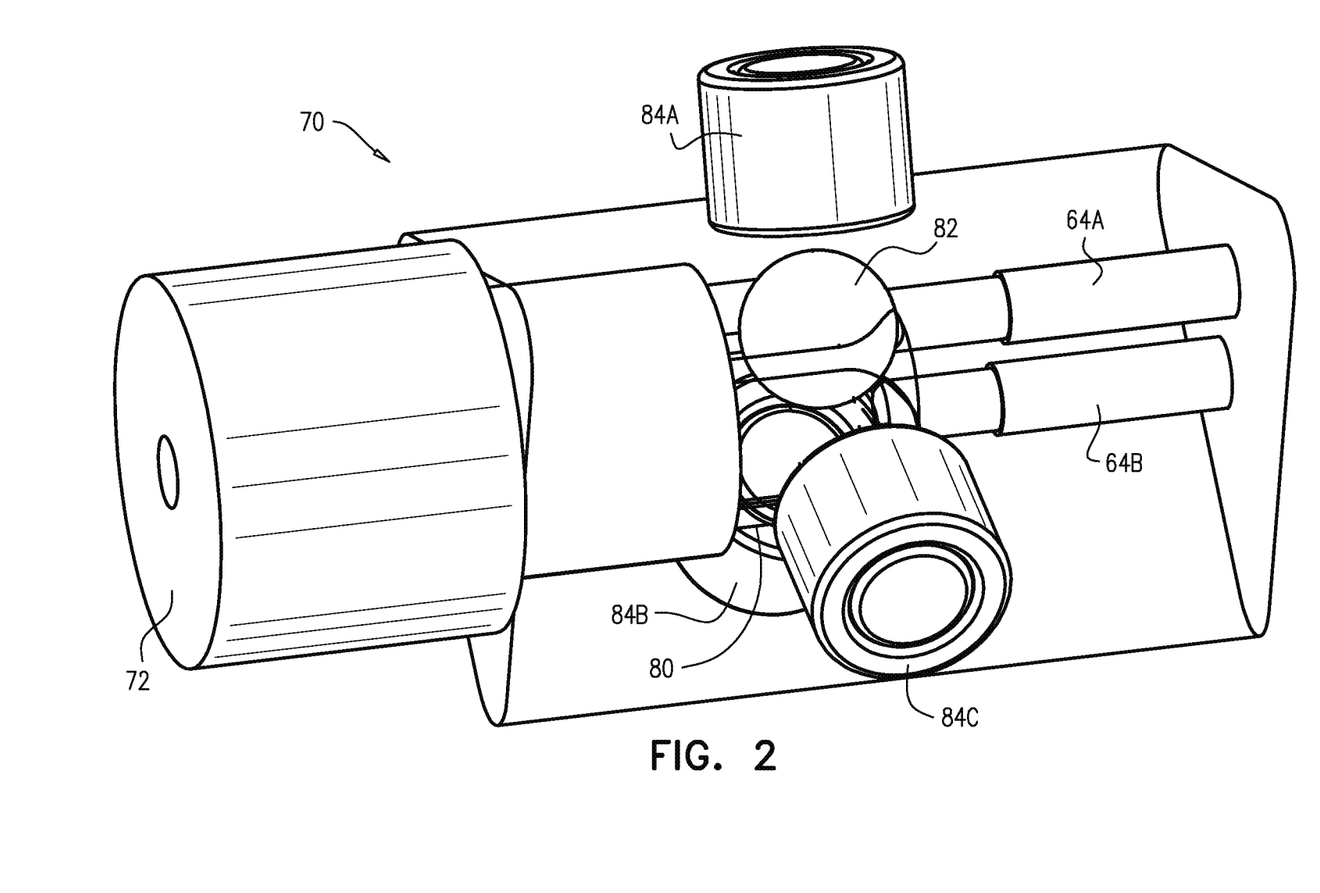
FIG. 2 is a schematic perspective view in a longitudinal direction of the manifold, in accordance with an embodiment of the present invention.
Figure 3A:
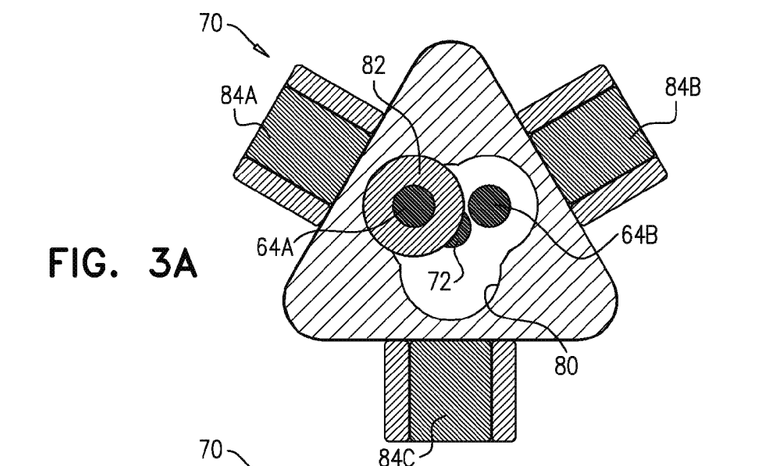
FIGS. 3A-3C are schematic cross-sectional latitudinal views of the manifold, in accordance with an embodiment of the present invention.
Figure 3B:
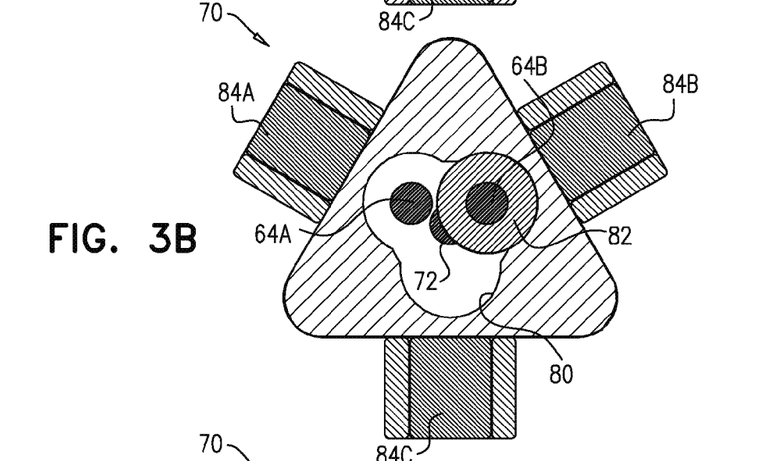
Figure 3C:
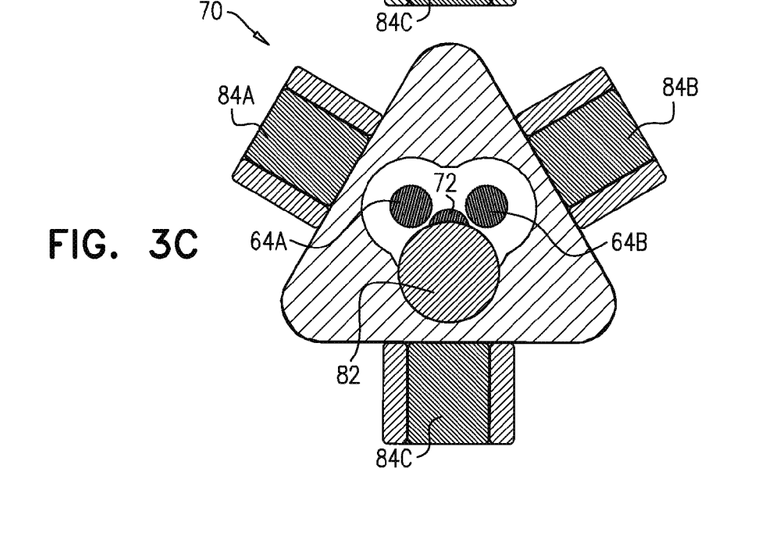

FIG. 2 is a schematic perspective view in a longitudinal direction of manifold 70, and FIGS. 3A-3C are schematic cross-sectional latitudinal views of manifold 70, in accordance with an embodiment of the present invention. Manifold 70 comprises a sealed chamber 80 in fluid communication with inlet tube 72 at a first end of the chamber and in fluid communication with outlet tubes 64A, 64B at a second end of the chamber. The outlet tubes deliver irrigation fluid to respective apertures of the manifold, in this case apertures 62A and 62B (FIG. 1).

A ball 82 is contained within chamber 80, and electromagnets 84 are disposed, typically symmetrically, outside chamber 80. In the example shown in FIGS. 2 and 3, electromagnets 84 may be differentiated by appending a letter to the identifying numeral so that the electromagnets comprise electromagnets 84A, 84B and 84C.

Ball 82 comprises a magnetic material such as steel, and electromagnets 84 are configured as a magnetic field generator that generates a variable magnetic field within chamber 80 so as to move the ball within the chamber. In embodiments of the present invention processor 44 can activate a given electromagnet 84 by conveying electrical power to the given electromagnet. Likewise, processor 44 can deactivate a given electromagnet 84 by halting the flow of electrical power to the given electromagnet. By positioning ball 82 inside chamber 80 and electromagnets 84 outside the chamber, embodiments of the present invention provide a sealed manifold, thereby preventing any foreign material from entering manifold 70 during a medical procedure.

In the example shown in FIG. 3A, processor 44 activates electromagnet 84A and deactivates electromagnets 84B and 84C, thereby moving ball 82 within chamber 80 to a first position so as to block outlet tube 64A. Manifold 70 is configured to block flow of irrigation fluid from inlet tube 72 to outlet tube 64A when ball 82 is located in the first position. When ball 82 is located in the first position, irrigation fluid from inlet tube 72 flows through apertures 62B via outlet tube 64B.

In the example shown in FIG. 3B, processor 44 activates electromagnet 84B and deactivates electromagnets 84A and 84C, thereby moving ball 82 within chamber 80 to a second position so as to block outlet tube 64B. Manifold 70 is configured to block flow of irrigation fluid from inlet tube 72 to outlet tube 64B when ball 82 is located in the second position. When ball 82 is located in the second position, irrigation fluid from inlet tube 72 flows through apertures 62A via outlet tube 64A.

In the example shown in FIG. 3C, processor 44 activates electromagnet 84C and deactivates electromagnets 84A and 84B, thereby moving ball 82 within chamber 80 to a third position so as to not to block outlet tubes 64A and 64B. When ball 82 is located in the third position, neither of the outlet tubes are blocked, so irrigation fluid from inlet tube 72 flows through apertures 62A via outlet tube 64A and through apertures 62B via outlet tube 64B.

Figure 4:
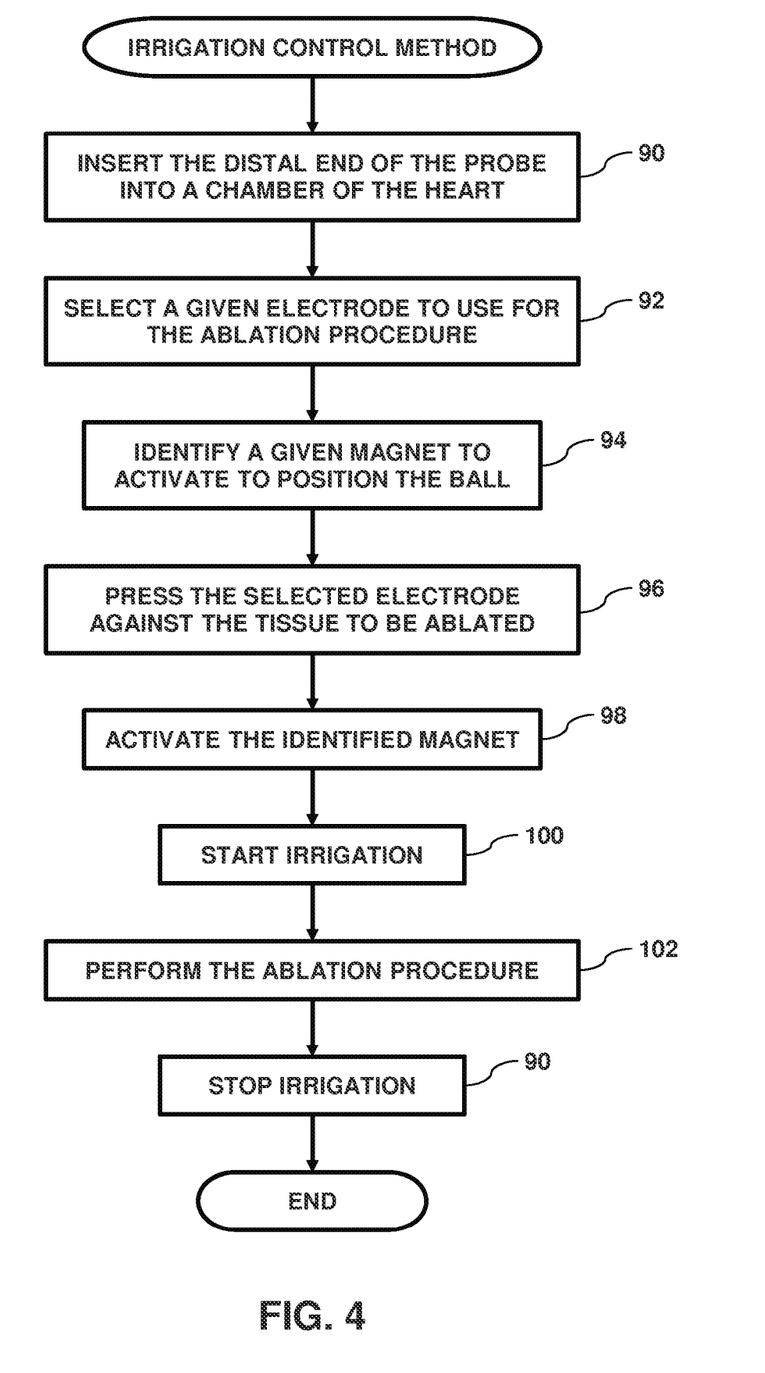
FIG. 4 is a flow diagram that illustrates a method of using the manifold to control irrigation during a cardiac ablation procedure, in accordance with an embodiment of the present invention.
Figure 5:
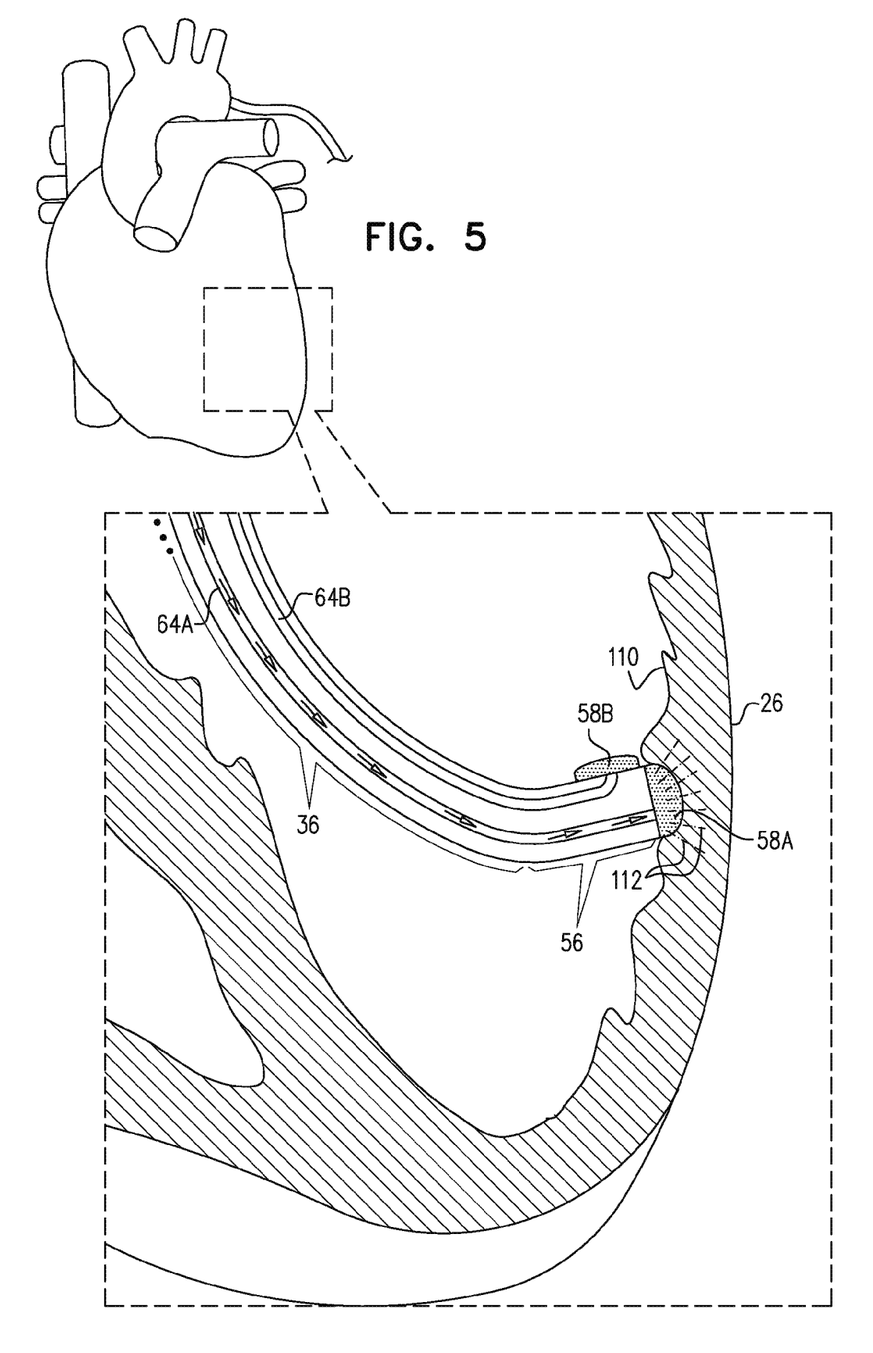
FIG. 5 is a schematic detail view showing a distal tip of a probe in contact with endocaridial tissue during the cardiac ablation procedure.

FIG. 4 is a flow diagram that illustrates a method of controlling irrigation during an ablation procedure, and FIG. 5 is a schematic detail view showing distal tip 56 in contact with endocardial tissue 110 during a cardiac ablation procedure, in accordance with an embodiment of the present invention. In an insertion step 90, operator 32 manipulates handle 30 in order to insert distal end 36 of probe 22 into a chamber of heart 26, and using input devices 52, the operator selects a given electrode 58 to perform an ablation procedure in a selection step 92.

In an identification step 94, processor 44 identifies a given electromagnet 84 that when activated, will move ball 82 to a position that allows irrigation fluid to flow to apertures 62 in the identified electrode. In a manipulation step 96, operator 32 manipulates handle 30 to position the selected electrode against the intracardiac tissue, and in an activation step 98, processor 44 activates the identified magnet, thereby moving ball 82 to one of the positions described supra.

Using the selected electrode, system 20 starts irrigating the intracardiac tissue via apertures 62 in a start step 100, performs the ablation procedure in an ablation step 102, stops the irrigation in a stop step 104, and the method ends. In the example shown in FIG. 5, processor 44 activates electromagnet 84B (as shown in FIG. 3B) in order to block outlet tube 64B, thereby directing irrigation fluid 112 through outlet tube 64A and apertures 62A, thereby irrigating the intracardiac tissue being ablated.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A system, comprising:
    a probe comprising a handle, the probe further comprising an insertion tube having a distal end and an insulating sheath:
    an inlet tube configured to receive an irrigation fluid from a pressurized fluid source;
    at least first and second outlet tubes configured to deliver the irrigation fluid to respective outlets of the device;
    a manifold located within the handle containing a chamber coupled between the inlet tube and at least the first and second outlet tubes;
    a ball comprising a magnetic material contained inside the chamber; and
    a magnetic field generator disposed outside the chamber and configured to generate a variable magnetic field within the chamber so as to move the ball between at least a first position in which the first outlet tube is blocked, a second position in which the second outlet tube is blocked, and a third position, in which neither of the outlet tubes is blocked, a plurality of ablation electrodes, the electrodes comprising thin metal layers formed over the insulating sheath of the insertion tube, wherein the respective outlets are connected to respective apertures of the ablation electrodes.

2. The system according to claim 1, wherein the irrigation fluid comprises a saline solution.

3. The system according to claim 1, wherein the magnetic material comprises steel.

4. The system according to claim 1, wherein the magnetic field generator comprises multiple electromagnets disposed outside the chamber.

5. The system according to claim 4, wherein the magnetic field generator is configured to generate the variable magnetic field by activating a given electromagnet.

6. A system comprising:

a probe comprising a handle, the probe further comprising an insertion tube having a distal end and an insulating sheath, an inlet tube configured to receive an irrigation fluid from a pressurized fluid source;

at least first and second outlet tubes configured to deliver the irrigation fluid to respective outlets of the device;

a manifold located within the handle containing a chamber coupled between the inlet tube and at least the first and second outlet tubes;

a ball comprising a magnetic material contained inside the chamber; and a magnetic field generator disposed outside the chamber and configured to generate a variable magnetic field within the chamber so as to move the ball between at least a first position in which the first outlet tube is blocked, a second position in which the second outlet tube is blocked, and a third position, in which neither of the outlet tubes is blocked, a plurality of ablation electrodes, the electrodes comprising thin metal layers formed over the insulation sheath of the insertion tube, wherein the respective outlets are connected to respective apertures of the ablation electrodes, wherein the magnetic field generator comprises multiple electromagnets disposed outside the chamber, and wherein the magnetic field generator is configured to generate the variable magnetic field by activating a given electromagnet.

* * * * *